(12) United States Patent
Kronström et al.

(10) Patent No.: US 10,687,730 B2
(45) Date of Patent: Jun. 23, 2020

(54) BIOIMPEDANCE SENSOR, STYLET, CANNULA AND METHOD FOR MEASURING BIOIMPEDANCE

(71) Applicant: INJEQ OY, Tampere (FI)

(72) Inventors: Kai Kronström, Espoo (FI); Petri Ahonen, Tampere (FI); Juho Kari, Tampere (FI); Riitta Seppänen, Espoo (FI)

(73) Assignee: INJEQ OY, Tampere (FI)

( * ) Notice: Subject to any disclaimer, the term of this patent is extended or adjusted under 35 U.S.C. 154(b) by 1117 days.

(21) Appl. No.: 14/780,067

(22) PCT Filed: Mar. 25, 2014

(86) PCT No.: PCT/IB2014/060120
§ 371 (c)(1),
(2) Date: Sep. 25, 2015

(87) PCT Pub. No.: WO2014/155282
PCT Pub. Date: Oct. 2, 2014

(65) Prior Publication Data
US 2016/0029920 A1     Feb. 4, 2016

(30) Foreign Application Priority Data
Mar. 28, 2013   (EP) .................................... 13161684

(51) Int. Cl.
*A61B 5/053*   (2006.01)
*A61B 5/00*    (2006.01)
*A61B 5/22*    (2006.01)

(52) U.S. Cl.
CPC .......... *A61B 5/0538* (2013.01); *A61B 5/6848* (2013.01); *A61B 5/225* (2013.01); *A61B 5/6846* (2013.01); *A61B 2560/0209* (2013.01)

(58) Field of Classification Search
CPC ......... A61B 5/05; A61B 5/053; A61B 5/6848; A61B 18/18; A61B 5/0531; A61B 5/0532;
(Continued)

(56) References Cited

U.S. PATENT DOCUMENTS 6,337,994 B1 * 1/2002 Stoianovici ............ A61B 5/053
                                                      433/27
6,770,070 B1 * 8/2004 Balbierz ................ A61B 10/04
                                                     600/566
(Continued)

FOREIGN PATENT DOCUMENTS

WO   WO 2006119245   11/2006
WO   WO 2009019707    2/2009
WO   WO 2009142918   11/2009

OTHER PUBLICATIONS

European Office Action in Application 14 722 734.2-1657, EPO, dated Oct. 27, 2017.
(Continued)

*Primary Examiner* — Eun Hwa Kim

(57) ABSTRACT

The objective of the invention is to make the use of a cannula belonging to a bioimpedance sensor easier in a medical procedure after defining the bioimpedance. The bioimpedance sensor (300) comprises a cannula (200) and a stylet (100) moveable in relation to it and is characterized in that: the cannula (200) comprises a needle tube (1), consisting of or containing electrically conductive material so that the cannula (200) is available for use as a needle electrode (1, 2) or as a part of it;
the stylet (100) has a bevelled head and comprises a number of stylet electrodes (5) surrounded by electrical insulation (13) in such a manner that the beveled head is left free from electrical insulation so that the advance of the needle tip can
(Continued)

be characterized by measuring the impedance between the needle electrode (1,2) and the number of stylet electrodes (5);

the stylet (100) is additionally equipped with at least one coupling piece (6) for the electrical coupling of the stylet (100) to the needle electrode (1, 2) inside the cannula (200), whereby the impedance between the needle electrode (1, 2) and at least one of the stylet electrodes (5) can be measured inside the bioimpedance sensor (300) and exclusively through the stylet (100).

The patent application contains independent claims also for the stylet, the cannula and the method for measuring bioimpedance.

23 Claims, 4 Drawing Sheets

(58) Field of Classification Search
CPC ... A61B 5/0533; A61B 5/0537; A61B 5/0538; A61B 5/061; A61B 5/063; A61B 5/068; A61B 2562/22; A61B 2562/225; A61B 2562/227

USPC .......................................................... 600/547
See application file for complete search history.

(56) References Cited

U.S. PATENT DOCUMENTS

| | | | |
|---|---|---|---|
| 7,918,852 B2* | 4/2011 | Tullis | A61B 18/1477 606/41 |
| 2002/0042594 A1* | 4/2002 | Lum | A61B 5/053 604/117 |
| 2004/0010204 A1 | 1/2004 | Weber | |
| 2010/0256483 A1 | 10/2010 | Wall | |
| 2011/0046618 A1* | 2/2011 | Minar | A61B 5/053 606/41 |

OTHER PUBLICATIONS

Search Report in Application EP13161684.9, dated Jul. 25, 2013, EPO.
International Report on Patentability in PCT Application, PCT/IB2014/06012, EPO, dated Sep. 9, 2015.

* cited by examiner

BIOIMPEDANCE SENSOR, STYLET, CANNULA AND METHOD FOR MEASURING BIOIMPEDANCE

TECHNICAL FIELD

The invention is related to medical devices and specifically to bioimpedance sensors.

BACKGROUND INFORMATION

Surgical needles are used in different medical procedures, for example for taking specimens or for injecting substances. The use of a cannula and a stylet (or stylus or mandrin) contained therein as electrodes for measuring bioimpedance is known from the U.S. Pat. No. 6,337,994 B1.

In an arrangement for measuring bioimpedance shown in the drawings of the U.S. Pat. No. 6,337,994 in FIG. 7, the electrical coupling of a needle electrode, formed by the cannula, and a stylet electrode of the stylet, moveable within the cannula, to an impedance meter is implemented by means of alligator clip connectors to be attached to the needle electrode and to the stylet electrode, which does not necessarily enable a reliable electrical coupling of the electrodes to the impedance meter when measuring bioimpedance, for example when preparing a medical procedure. After measuring the bioimpedance, the line leading from the cannula to the impedance meter may hinder the work when the cannula is meant to be used for taking specimens or for injecting a substance. In this case, it is possible to disconnect the line, however, disconnecting the alligator clip connectors from the cannula is laborious and increases the risk involved in the procedure to be carried out using the cannula. This is, among other things, due to the fact that when removing the alligator clip connectors, the cannula may tend to shift from its defined position.

The applicant's Finnish patent 123246 describes an arrangement for measuring bioimpedance, whereby only the electrodes of the electrode pattern contained in the stylet are used for measuring bioimpedance. The wiring for measuring bioimpedance can be easily removed by means of the measurement arrangement used in the patent 123246 because the cannula is not used as an electrode. However, the measurement arrangement presented in the patent is not fit for use in a situation in which the cannula must be used as the other measuring electrode or as one of the measuring electrodes.

SUMMARY OF THE INVENTION

One objective of the invention is to enable the measurement of bioimpedance more easily than the known technology in an arrangement for measuring bioimpedance, whereby a cannula is used as the other electrode or as one of the electrodes.

The bioimpedance sensor comprises a cannula and a stylet moveable in relation to it. The cannula comprises a needle tube which consists of or which contains electrically conductive material so that the cannula is available for use as a needle electrode or as a part of it.

The stylet has a bevelled head and comprises a number of stylet electrodes surrounded by electrical insulation in such a manner that the bevelled head is left free from electrical insulation so that the advance of the needle tip can be characterized by measuring the impedance between the needle electrode and the number of stylet electrodes. Moreover, the stylet is equipped with at least one coupling piece for the electrical coupling of the stylet to the needle electrode inside the cannula, whereby the impedance between the needle electrode and at least one of the stylet electrodes is measurable inside the bioimpedance sensor and exclusively through the stylet.

When it is desired to make the cannula operational, for example for taking specimens or for injecting a substance, and the measurement wiring used for measuring the bioimpedance must be removed, after measuring the bioimpedance by means of the bioimpedance sensor presented here, it is only necessary to remove the stylet from the bioimpedance sensor.

With the coupling piece of the stylet being configured to create a galvanic coupling through an adapter attached or connected to the needle tube, the electrical contact point or the electrical contact points are better protected from extrinsic factors. It is thus possible to ensure that the contact is interference-free.

With the adapter being tapered and dimensioned in such a way that the coupling piece of the stylet makes an electrical contact with the adapter while the stylet is positioned within the cannula, the electrical contact can be ensured by pushing the stylet deep enough.

In an especially advantageous embodiment the adapter is funnel-shaped. This does not only make it easier to make an electrical contact from the needle electrode to the stylet but also contributes to the use of the cannula in injections viz. the funnel shape enables to increase the injection pressure and quantity or to reduce the travel of the piston used in injection. In addition, the funnel shape is important because the stylet or catheter to be pushed into the cannula does not bump against a threshold while being pushed into the hub of the cannula.

With the first clearance located farther away from the needle tube of the adapter and the smaller clearance located nearer to the needle tube being connected by means of a bevel part, the wedging effect thus created can be used for ensuring the making of electrical contact.

With the coupling piece of the stylet containing a tubular or split piece, the electrical contact can be achieved over a wider range and possibly at least partly in a rotationally symmetrical way, whereby it is possible to eliminate the significance of the stylet's angle of rotation when pushing the stylet into the cannula. This improves the operational reliability of the sensor for measuring bioimpedance.

With the tubular or split piece of the coupling piece and the adapter being adapted to each other in such a way that the coupling piece yields while the stylet is being pushed into the cannula, the elasticity occurring during yielding of the coupling piece can be utilized for ensuring the electrical contact because, due to the resilience, an adequate contact force can be obtained.

A stylet according to the second aspect of the invention to be used in a bioimpedance sensor according to the first aspect of the invention has a bevelled head and comprises a number of stylet electrodes surrounded by electrical insulation and arranged to the bevelled head. The stylet is additionally equipped with at least one coupling piece for the electrical coupling of the stylet to a needle electrode inside the cannula, whereby the impedance between the needle electrode and at least one of the stylet electrodes can be measured inside the bioimpedance sensor and exclusively through the stylet.

With such a stylet it is only necessary to remove the stylet from the bioimpedance sensor after measuring the bioimpedance when it is desired to make the cannula operational, for example for taking specimens or for injecting a substance, and the measurement wiring used for measuring bioimpedance must be removed.

The coupling piece preferably contains a tubular piece or a split one. It is thus possible to form a perfectly well functioning functional bioimpedance-sensor block, especially when the cannula has a funnel-shaped adapter within which the galvanic contact is made.

According to the third aspect of the invention, a bioimpedance sensor according to the first aspect of the invention is used in the method for measuring bioimpedance by means of a bioimpedance sensor, comprising a cannula and a stylet moveable in relation to it, and the bioimpedance is measured exclusively through the stylet between the needle electrode and at least one of the stylet electrodes. The method enables to use the cannula forming part of the bioimpedance sensor without any disturbing needle electrode wiring and without the needle electrode wiring having to be removed separately because, in this case, the needle electrode wiring is already removed when the stylet is removed from the cannula.

The cannula suitable for use in a bioimpedance sensor comprises i) a needle tube, consisting of or containing electrically conductive material so that the cannula is available for use as a needle electrode or as a part of it, and ii) an adapter, attached or connected to the needle electrode by means of galvanic coupling, comprising at least two successive funnel-shaped structures, of which the larger diameter of the funnel-shaped structure located closer to the free end of needle tube is greater than the larger diameter of the funnel-shaped structure located farther away from the free end of needle tube. The two funnel-shaped structures that should at least be contained in the adapter help to position the stylet or even a catheter possibly used in the cannula, especially if the stylet or the catheter is not quite straight.

The simplest technical method to implement funnel-shaped structures is by means of drilling. The adapter is most preferably within the hub. The operation of the adapter can thus be protected in the best possible way against extrinsic factors and contamination.

BRIEF DESCRIPTION OF THE DRAWINGS

These and other features and advantages of the present invention will be better understood by reading the following detailed description, taken together with the drawings wherein.

The same reference numbers are used to refer to the same technical features in all FIGS.

DETAILED DESCRIPTION OF THE PREFERRED EMBODIMENTS

Figure 1:
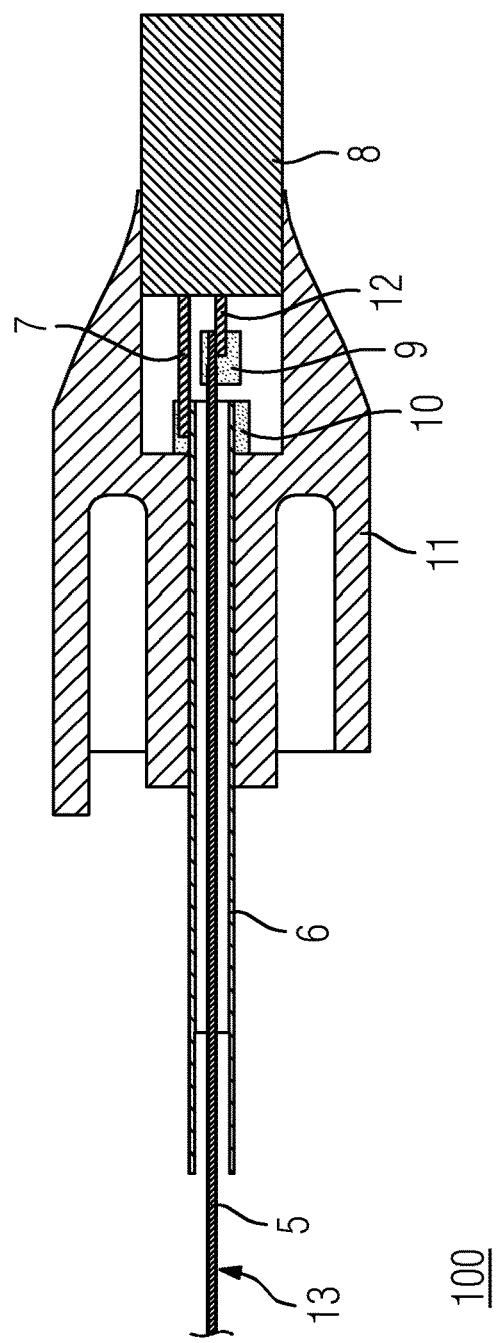
FIG. 1 is a cross-sectional view of the stylet in the longitudinal direction.

FIG. 1 shows a cross-section of stylet 100 in the longitudinal direction. Stylet 100 comprises an electrode wire 5, an electrical insulation 13 surrounding the electrode wire 5 as well as a metal tube 6 functioning as a coupling piece.

In addition to these, the stylet 100 comprises a handle 11, which most preferably surrounds both the metal tube 6 and the electrode wire 5.

Inside the handle 11 there is most preferably a recess or an opening in which the attachment of the metal tube 6 to a conductor 7 and the attachment of the electrode wire 5 to a conductor 12 is carried out. The attachment can be carried out for example by soldering, by compressing or by using an electrically conductive adhesive.

In the embodiment shown in FIG. 1, the electrical contact between the conductor 7 and the metal tube 6 is ensured by applying an electrically conductive adhesive 10 around the metal tube 6 in such a way that the conductor 7 is adhered to it. The attachment of the conductor 12 to the electrode wire 5 is ensured by applying an electrically conductive adhesive 9 around the electrode wire 5 in such a way that the conductor 12 is adhered to it. The conductors 7 and 12 run within a cable 8.

Figure 2:
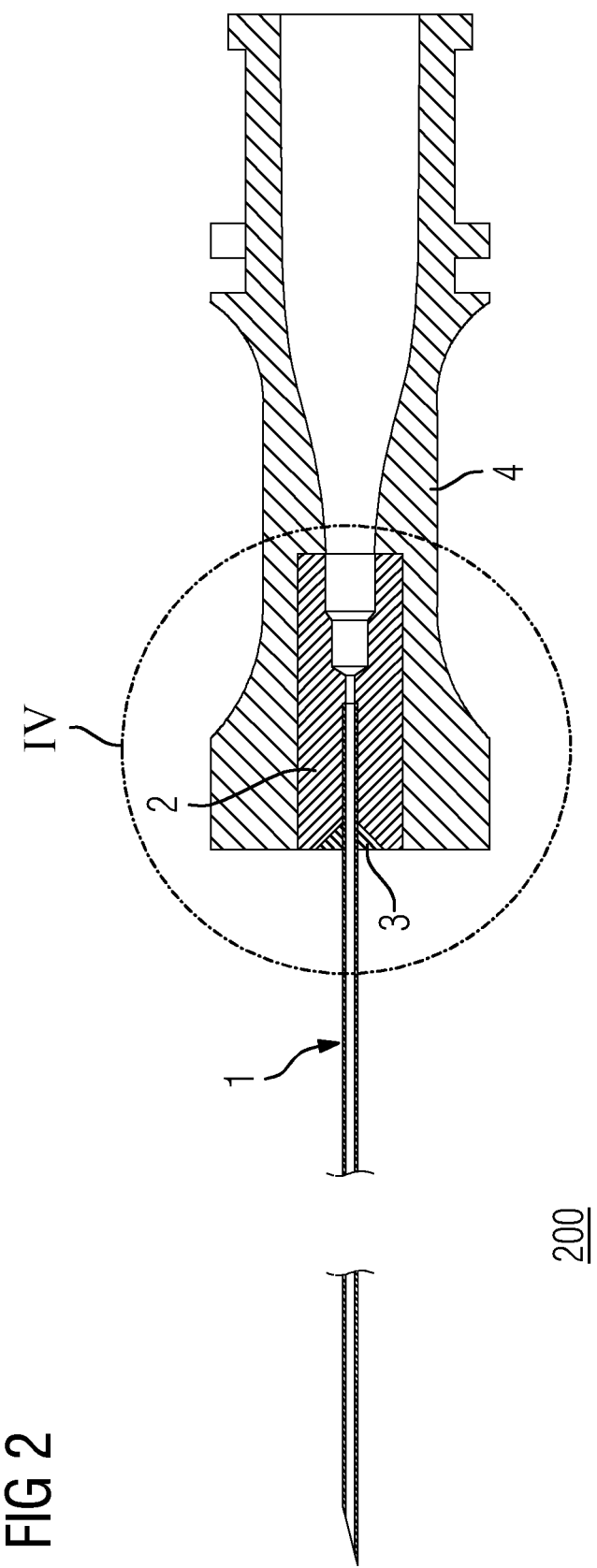
FIG. 2 is a cross-sectional view of the cannula in the longitudinal direction.
Figure 4:
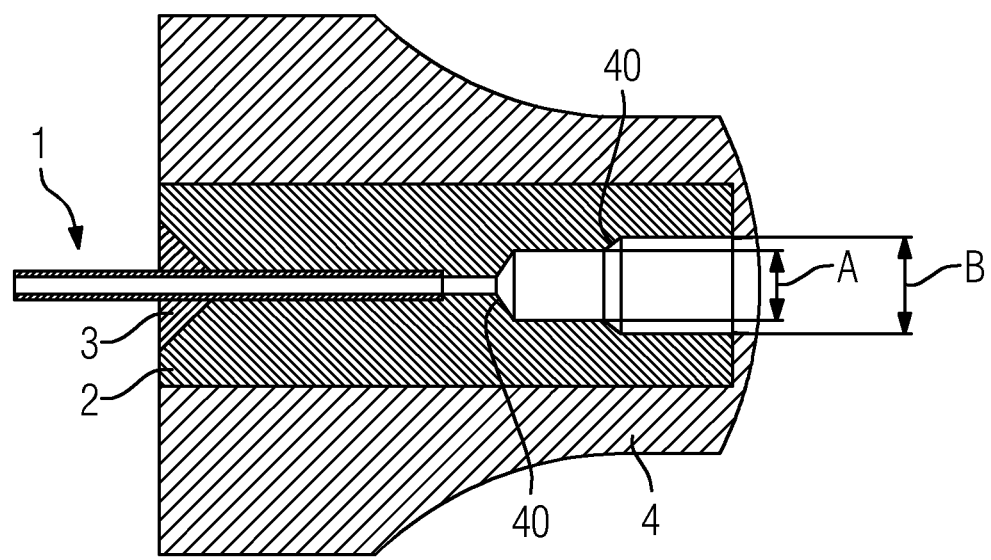
FIG. 4 is a more detailed representation of detail IV of the needle shown in FIG. 2.

FIG. 2 shows a cross-section of a cannula 200 in the longitudinal direction. A more detailed representation of the detail IV is shown in the drawing in FIG. 4.

The cannula 200 comprises a metallic needle tube 1, a metallic adapter 2 and the actual hub 4. The adapter 2 is most preferably attached to the hub by means of adhesive 3.

Figure 3:
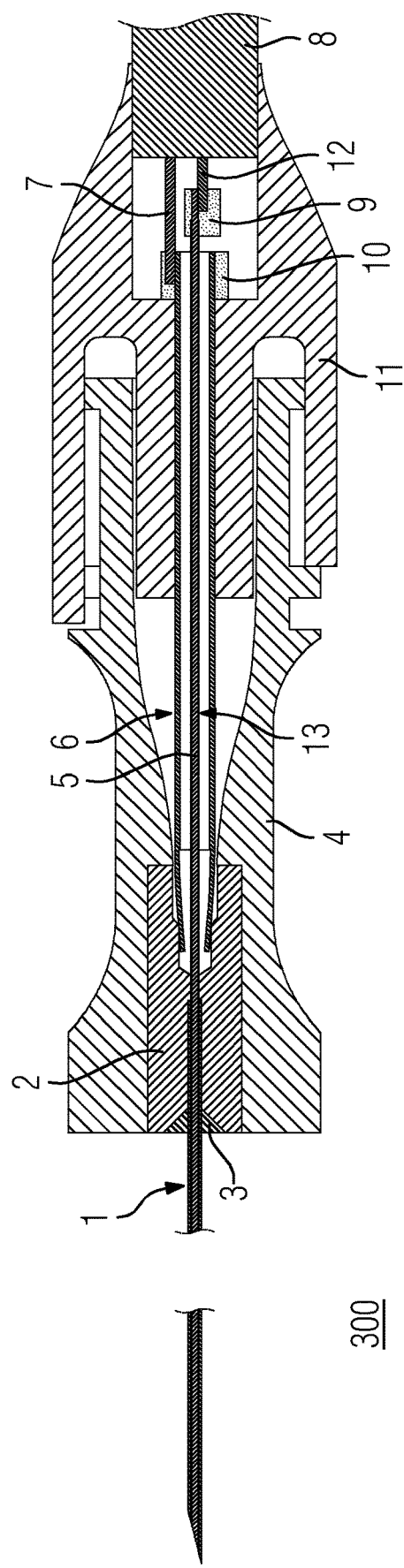
FIG. 3 is a cross-sectional view of the bioimpedance sensor in the longitudinal direction.

FIG. 3 shows sensor 300 for measuring bioimpedance, formed by the stylet 100 located within the cannula 200. The needle tube 1 in the measurement sensor 300 functions as a needle electrode. The needle tube 1 being made of metal and being galvanically coupled to the metallic adapter 2, the adapter 2 and the needle electrode are in the same potential.

The electrode wire 5 of stylet 100 FIG. 1 functions as a stylet electrode.

By measuring the impedance between the needle electrode and the stylet electrode through the cable 8, it is possible to characterize the advance of the needle tip, i.e. the distal end of needle tube 1, and the distal end of electrode wire 5 within the tissue by means of impedance spectrum or impedance variation characteristic of each tissue layer and type in a way known as such from the state of the art, for example by using the method described in the U.S. Pat. No. 6,337,994.

As soon as the needle tip has reached the right position, the stylet 100 is removed from the cannula 200. By doing so, the cable 8 is also removed and will not interfere with further procedures. After this, the cannula 200 is ready for use in a medical procedure.

Detail IV (FIG. 4) shows how the clearance B of adapter 2 can be tapered to clearance A by means of the bevel part 40 included in the adapter 2. The adapter will thus become funnel-shaped. Especially when the metal tube 6 is a split tube, it can be pushed easily into the adapter 2. The metal tube 6 forms a galvanic contact to the adapter 2 so that it is in the same potential with the needle electrode.

Due to the arrangement presented here, the invention is able to make an electrical contact between the stylet and the cannula without a separate removable line. Due also to the funnel-shaped adapter 2, we are able to fit the needle tubes 1 of different sizes together with a standard-sized stylet 100. Moreover, we are able to strengthen the structure by means of the adapter 2.

In other words, the removable stylet 100 is pushed into the funnel-shaped adapter 2 with the task of preventing the tissues from being pushed inside the cannula 200 and, in some cases, also of strengthening the needle. The stylet 100, on the other hand, is also used at least as one electrode.

The needle according to the preferred embodiment of the invention has been adapted in such a way that the electrical contact between the needle tube 1 and the adapter 2 has been ensured, for example by using an adequately accurate fit, coatings or a small amount of electrically conductive adhesive 3. In addition, the end of the adapter 2 guiding the thrust of stylet 100 has been implemented for example by means of two drillings in such a way that diameter A is smaller than diameter B with the bevel part 40 located between them. If required, the adapter 2 can be coated to improve the electrical contact.

The split tube 6 whose outer diameter has been chosen appropriately between [A, B] is added to the stylet 100. The tube 6 can be coated (for example gold-plated) to improve the electrical contact. When the stylet 100 is pushed inside the cannula 200, a galvanic contact is made between the adapter 2 and the tube 6. As to the tube 6, it has been connected as a part of the stylet 100 according to FIG. 1 and, for example by means of a conductive adhesive 10, to a conductor or a coupler through which the cannula 100 can be coupled to an impedance meter. Moreover, the stylet 100 has one or several electrodes as a part of the stylet 100.

As an alternative, the electrical contact can be made to the outer surface, the inner surface or the end of needle tube 1 or to a piece to be attached to the needle tube.

The stylet 100 to be connected to the cannula 200 closes it and, at the same time, it functions as a plug enabling an electrical contact to the cannula 100. The electrical contact is disconnected as soon as the stylet 100 is removed.

There may be several electrodes in the stylet 100, for example in the way described in the Finnish patent 123246.

The above description of advantageous embodiments is only exemplary. The invention may differ within the scope of patent claims and their legally equivalent embodiments.

It should be noted in particular that the bioimpedance sensor 300 and the stylet 100 can also be combined with a cannula which does not contain at least two successive funnel-shaped structures of which the larger diameter of the funnel-shaped structure located closer to the free end of the needle tube is greater than the larger diameter of the funnel-shaped structure located farther away from the free end of the needle tube.

Most advantageously, the bioimpedance sensor 300 is connected to a metering instrument by means of electric lines starting from either the stylet 100. In addition to this or as an alternative to this, the stylet 100 may have a connector for electrical lines and/or for a small-sized metering instrument. At the end of the stylet 100, there may be for example a double-pole DC connector, to which the electrical lines are connected. The metering instrument can even be connected directly to the stylet 100 and/or implemented as part of it.

The objective of the invention is to make the use of a cannula belonging to a bioimpedance sensor easier in a medical procedure after defining the bioimpedance. The bioimpedance sensor (300) comprises a cannula (200) and a stylet (100) moveable in relation to it and is characterized in that:
the cannula (200) comprises a needle tube (1), consisting of or containing electrically conductive material so that the cannula (200) is available for use as a needle electrode (1, 2) or as a part of it;
the stylet (100) has a beveled head and comprises a number of stylet electrodes (5) surrounded by electrical insulation (13) in such a manner that the beveled head is left free from electrical insulation so that the advance of the needle tip can be characterized by measuring the impedance between the needle electrode (1, 2) and the number of stylet electrodes (5);
the stylet (100) is additionally equipped with at least one coupling piece (6) for the electrical coupling of the stylet (100) to the needle electrode (1, 2) inside the cannula (200), whereby the impedance between the needle electrode (1, 2) and at least one of the stylet electrodes (5) can be measured inside the bioimpedance sensor (300) and exclusively through the stylet (100).

The patent application contains independent claims also for the stylet, the cannula and the method for measuring bioimpedance.

Modifications and substitutions by one or ordinary skill in the art are considered to be within the scope of the present invention which is not to be limited except by the allowed claims and their legal equivalents.

The invention claimed is:

1. A bioimpedance sensor (300), comprising a cannula (200) and a stylet (100), in use, said stylet (100) configured for being linearly insertable into and removable from said cannula (200), said bioimpedance sensor (300) configured for measuring human tissue impedance, wherein:
the cannula (200) includes an electrically conductive hollow needle tube (1) having a beveled distal end portion, said electrically conductive hollow needle tube (1) configured for use as a needle electrode;
the stylet (100) has a beveled distal end portion and comprises a handle (11) portion and an electrode wire (5) surrounded by electrical insulation (13) extending from said handle portion (11), said electrode wire (5) having a beveled distal end portion and configured for functioning as a stylet electrode;
the stylet (100) includes at least one coupling piece (6), configured for electrically coupling a conductor (7) disposed in said handle portion (11) of said stylet (100) to the electrically conductive hollow needle tube (1) of the cannula (200), wherein the at least one coupling piece (6) of the stylet (100) is a resilient hollow metal structure configured to yield in a cross-sectional direction perpendicular to a longitudinal direction of the resilient hollow metal structure when pushed inside a metalized tapering portion inside an adapter (2) electrically coupled to the electrically conductive hollow needle tube (1) in the cannula (200) and configured, by the yielding of the resilient hollow metal structure with sufficient contact force against the metalized tapering portion inside the adapter (2) in the cannula (200), to create a galvanic electrical coupling to the electrically conductive hollow needle tube (1) through the adapter (2); and
wherein the electrode wire (5) of said stylet (100) and the conductor (7) of the handle of the stylet (100) electrically coupled to said electrically conductive hollow needle tube (1) of the cannula (200) are electrically coupled to an electrical cable (8) such that the impedance between the electrically conductive hollow needle tube (1) disposed in the cannula (200) and the electrode wire (5) of said stylet (100) is measurable from the electrical cable (8) such that the advance and location of the beveled distal end portion of the bioimpedance sensor (300) comprising said stylet (100) linearly inserted into said cannula (200) within the human tissue at the beveled distal end portion of the bioimpedance sensor (300) can be determined by means of an impedance measurement of the human tissue between said beveled distal end portion of the needle tube (1) and the co-linear and co-planar beveled distal end portion of the electrode wire (5) of the stylet (100) inserted into the cannula (200).

2. The bioimpedance sensor (300) according to claim 1, wherein the metalized tapering portion inside the adapter (2) is funnel-shaped.

3. The bioimpedance sensor (300) according to claim 2, wherein the funnel-shaped metalized tapering portion inside the adapter (2) comprises at least two successive funnel-shaped structures (40) of which a diameter (A) of one of the two successive funnel-shaped structures (40) located closer to a proximal end of the needle tube (1) is smaller in diameter than a diameter (B) of one of the two successive funnel shaped structures (40) located farther away from the proximal end of the needle tube (1).

4. The bioimpedance sensor (300) according to claim 3, wherein a first diameter (B) of one of the two successive funnel shaped structures (40) located farther away from the proximal end of the needle tube (1) of cannula (200) and a smaller diameter (A) of one of the two successive funnel shaped structures (40) located closer to the proximal end of the needle tube (1) are connected to each other by means of a bevel part (40).

5. The bioimpedance sensor (300) according to claim 1, wherein the at least one coupling piece (6) of the stylet (100) is one of a tubular or split tube coupling piece (6).

6. The bioimpedance sensor (300) according to claim 5, wherein the tubular or split piece of the at least one coupling piece (6) and the adapter (2) are configured in such a way that the at least one coupling piece (6) yields while the stylet (100) is being pushed into the cannula (200).

7. The bioimpedance sensor (300) according to claim 1, wherein the at least one coupling piece (6) includes a metallic coating.

8. The bioimpedance sensor (300) according to claim 7, wherein the metallic coating is a gold coating.

9. The bioimpedance sensor (300) according to claim 1, wherein the metallized tapering portion inside the adapter (2) includes a metallic coating.

10. The bioimpedance sensor (300) according to claim 9, wherein the metallic coating is a gold coating.

11. The bioimpedance sensor (300) according to claim 1, wherein the funnel-shaped metalized tapering portion inside the adapter (2) is formed by drilling.

12. The bioimpedance sensor (300) according to claim 3, wherein the funnel-shaped metalized tapering portion inside the adapter (2) is formed by drilling in two different diameters.

13. A bioimpedance sensor (300), comprising a cannula (200) and a stylet (100), in use, said stylet (100) configured for being linearly insertable into and removable from said cannula (200), said bioimpedance sensor (300) configured for measuring human tissue impedance, wherein:

the cannula (200) includes an electrically conductive hollow needle tube (1) having a beveled distal end portion, said electrically conductive hollow needle tube configured for use as a needle electrode (1);

the stylet (100) has a beveled distal end portion and comprises a handle (11) portion and an electrode wire (5) surrounded by electrical insulation (13) extending from said handle portion (11), said electrode wire (5) having a beveled distal end portion and configured for functioning as a stylet electrode;

the stylet (100) includes at least one coupling piece (6), configured for electrically coupling a conductor (7) disposed in said handle portion (11) of said stylet (100) to the electrically conductive hollow needle tube (1) of the cannula (200), wherein the at least one coupling piece (6) of the stylet (100) is a resilient hollow or split hollow tubular metal structure configured to yield in a cross-sectional direction perpendicular to a longitudinal direction of the resilient hollow metal structure when pushed inside a metalized tapering recess inside an adapter (2) electrically coupled to the electrically conductive hollow needle tube (1) in the cannula (200) and configured, by the yielding of the resilient metal structure (6) with sufficient contact force against the metalized tapering recess inside the adapter (2) in the cannula (200), to create a galvanic electrical coupling to the electrically conductive hollow needle tube (1) through the adapter (2); and wherein the electrode wire (5) of said stylet (100) and the conductor (7) in the stylet handle electrically coupled to said electrically conductive hollow needle tube (1) of the cannula (200) are electrically coupled to an electrical cable (8) such that the impedance between the needle electrode (1) disposed in the cannula (200) and the electrode wire (5) of said stylet (100) is measurable from the electrical cable (8) such that the advance and location of the beveled distal end portion of the bioimpedance sensor (300) comprising said stylet (100) linearly inserted into said cannula (200) within the human tissue at the beveled distal end portion of the bioimpedance sensor (300) can be determined by means of an impedance measurement of the human tissue between said beveled distal end portion of the needle tube (1) and the co-linear and co-planar beveled distal end portion of the electrode wire (5) of the stylet (100) inserted into the cannula (200).

14. The bioimpedance sensor (300) according to claim 13, wherein the metalized tapering recess inside the adapter (2) is funnel-shaped.

15. The bioimpedance sensor (300) according to claim 14, wherein the funnel-shaped metalized tapering structure inside the adapter (2) is tapered and dimensioned in such a way that the coupling piece (6) of the stylet (100) makes an electrical contact with the adapter (2) while the stylet (100) is positioned inside the cannula (200).

16. The bioimpedance sensor (300) according to claim 13, wherein the at least one coupling piece (6) includes a metallic coating.

17. The bioimpedance sensor (300) according to claim 16, wherein the metallic coating is a gold coating.

18. The bioimpedance sensor (300) according to claim 13, wherein the metalized tapering recess inside the adapter (2) includes a metallic coating.

19. The bioimpedance sensor (300) according to claim 18, wherein the metallic coating of the metallized tapering recess inside the adapter (2) is a gold coating.

20. The bioimpedance sensor (300) according to claim 13, wherein the metalized tapering recess inside the adapter (2) is formed by drilling.

21. The bioimpedance sensor (300) according to claim 13, wherein the metalized tapering recess inside the adapter (2) comprises at least two successive funnel-shaped structures (40) of which a diameter (A) of one of the two successive funnel-shaped structures (40) located closer to a proximal end of the needle tube (1) is smaller in diameter than a diameter (B) of one of the two successive funnel shaped structures (40) located farther away from the proximal end of the needle tube (1).

22. The bioimpedance sensor (300) according to claim 21, wherein the metalized tapering recess inside the adapter (2) is formed by drilling in two different diameters.

23. The bioimpedance sensor (300) according to claim 22, wherein a first diameter (B) of one of the two successive funnel shaped structures (40) located farther from the proximal end of the needle tube (1) of cannula (200) and a smaller diameter (A) of one of the two successive funnel shaped structures (40) located closer to the proximal end of the needle tube (1) are connected to each other by means of a bevel part (40).

\* \* \* \* \*